(12) United States Patent
Kovvali et al.

(10) Patent No.: US 12,084,640 B2
(45) Date of Patent: Sep. 10, 2024

(54) AUTONOMOUS SUBMERSIBLE DEVICE FOR ALGAE GROWTH AND COLLECTION

(71) Applicant: ExxonMobil Technology and Engineering Company, Annandale, NJ (US)

(72) Inventors: Anjaneya S Kovvali, Herndon, VA (US); Everett J O'Neal, Asbury, NJ (US); Patrick L Hanks, Bridgewater, NJ (US); Mark A Deimund, Jersey City, NJ (US); Vinit Choudhary, Cypress, TX (US); Yesim Igci, Mountainside, NJ (US); Louis R Brown, La Jolla, CA (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 693 days.

(21) Appl. No.: 17/082,074

(22) Filed: Oct. 28, 2020

(65) Prior Publication Data
US 2021/0204500 A1 Jul. 8, 2021

Related U.S. Application Data

(60) Provisional application No. 62/938,430, filed on Nov. 21, 2019.

(51) Int. Cl.
*A01G 33/00* (2006.01)
*C12M 1/00* (2006.01)
*C12M 1/02* (2006.01)

(52) U.S. Cl.
CPC .......... *C12M 1/002* (2013.01); *C12M 27/00* (2013.01); *A01G 33/00* (2013.01)

(58) Field of Classification Search
CPC ....... C12M 1/002; C12M 27/00; A01G 33/00; Y02A 40/80; Y02A 90/40
See application file for complete search history.

(56) References Cited

U.S. PATENT DOCUMENTS

| | | | |
|---|---|---|---|
| 4,438,591 A * | 3/1984 | Kessler | C12N 1/02 47/1.4 |
| 6,842,931 B2 | 1/2005 | Porat et al. | |
| 8,869,337 B2 | 10/2014 | Sumonthee | |
| 2009/0301522 A1 * | 12/2009 | Abehasera | E04H 4/1654 134/18 |

(Continued)

FOREIGN PATENT DOCUMENTS

| | | | | |
|---|---|---|---|---|
| CN | 103103128 A | * | 5/2013 | |
| CN | 107900278 A | * | 4/2018 | ............... B22C 5/00 |

(Continued)

*Primary Examiner* — Liban M Hassan
(74) *Attorney, Agent, or Firm* — Shook, Hardy & Bacon L.L.P.

(57) ABSTRACT

A submersible device submersible within an algae slurry contained within a pond of an algae bioreactor, the submersible device including a drive motor operable to actuate one or more driven devices that move the submersible device within the pond, a circulation device operable to circulate the algae slurry through the submersible device and discharge the algae slurry back into the pond from a discharge port provided on the submersible device, and a computer system that controls operation of the drive motor and the circulation device.

17 Claims, 3 Drawing Sheets

(56) References Cited

U.S. PATENT DOCUMENTS

| | | | |
|---|---|---|---|
| 2010/0224574 A1* | 9/2010 | Youngs | B01D 33/646 210/780 |
| 2011/0136212 A1* | 6/2011 | Parsheh | C12M 41/26 435/296.1 |
| 2018/0142487 A1* | 5/2018 | Durvasula | F04D 29/708 |

FOREIGN PATENT DOCUMENTS

| | | | |
|---|---|---|---|
| CN | 208860838 U | * | 5/2019 |
| RU | 154521 U1 | * | 8/2015 |

* cited by examiner

AUTONOMOUS SUBMERSIBLE DEVICE FOR ALGAE GROWTH AND COLLECTION

CROSS-REFERENCE TO RELATED APPLICATIONS

This applications claims the benefit of priority from U.S. Provisional Application No. 62/938,430 filed Nov. 21, 2019, the contents of which are herein incorporated by reference in their entirety.

BACKGROUND OF THE INVENTION

Concerns about climate change, carbon dioxide ($CO_2$) emissions, and depleting mineral oil and gas resources have led to widespread interest in the production of biofuels from algae, including microalgae. As compared to other plant-based feedstocks, algae have higher $CO_2$ fixation efficiencies and growth rates, and growing algae can efficiently utilize wastewater, biomass residue, and industrial gases as nutrient sources. Algae are photoautotrophic organisms that can survive, grow, and reproduce with energy derived from the sun through the process of photosynthesis. Photosynthesis is essentially a carbon recycling process through which inorganic $CO_2$ combines with solar energy, other nutrients, and cellular biochemical processes to output gaseous oxygen and to synthesize carbohydrates and other compounds critical to the life of the algae.

Algae biomass is generally grown in a water slurry contained in a bioreactor system. Algae bioreactors are sometimes referred to as "photobioreactors" since they utilize a light source to cultivate photoautotrophic organisms. The most common types of bioreactors used in algal cultivation are open raceway ponds and tubular-type enclosed or open reactors. The water slurry within the bioreactor must be continuously mixed or agitated to ensure the algae are properly suspended within the water slurry and exposed to the light source for photosynthesis. When algae are grown in open raceway ponds, paddlewheel mixers are used to keep the algae slurry circulating and the algae suspended within the slurry, but ash and other particles and debris can collect near the ends of the raceway ponds. To prevent flow maldistribution or other issues with algae growth, algae raceway ponds require periodic cleaning to remove accumulated ash and debris.

Based on several factors, including penetration of solar radiation and excessive oxygen concentration (which inhibits algae growth), typical algae concentration in the water slurry reaches approximately 1000 ppm before it is suitable for harvesting. Harvesting from algae raceway ponds requires the entire water volume to be transported to a harvesting facility where the algae are separated from the water for further processing. Various processing methods separate the algal biomass from the water and extract lipids (oils) for the production of fuel and other oil-based products. The remaining wastewater and biomass residue can be recycled or otherwise used in a variety of sustainable applications. For example, the wastewater can form some or all of a subsequent water slurry and the biomass residue can be used as animal feed.

The energy consumption for algae growth, mixing, and harvesting can be significant. Because processing of algal biomass produces valuable commodities, including sustainable biofuels, cost-effective and energy-efficient harvesting methods that overcome some or all of the complications traditionally associated with the growth and harvesting of algae are desirable.

SUMMARY OF THE INVENTION

The present disclosure is related to algae cultivation for the production of biofuels and, more particularly, to a mixing and/or collection device submersible in an algae slurry of an algae bioreactor and operable to mix and aerate the algae slurry while filtering out particulate matter and harvesting algae of a predetermined size.

In one or more aspects of the disclosure, an algae bioreactor is disclosed and includes a pond that contains an algae slurry comprising at least water and algae, and a submersible device submersible within the algae slurry and including a drive motor operable to actuate one or more driven devices that move the submersible device within the pond, a circulation device operable to circulate the algae slurry through the submersible device and discharge the algae slurry back into the pond from a discharge port provided on the submersible device, and a computer system that controls operation of the drive motor and the circulation device. A photobioreactor is disclosed that includes one or more annular chambers concentrically positioned about a central axis, and an algae slurry contained within the one or more annular chambers.

In one or more additional aspects of the disclosure, a submersible device submersible within an algae slurry contained within a pond of an algae bioreactor is disclosed, the submersible device including a drive motor operable to actuate one or more driven devices that move the submersible device within the pond, a circulation device operable to circulate the algae slurry through the submersible device and discharge the algae slurry back into the pond from a discharge port provided on the submersible device, and a computer system that controls operation of the drive motor and the circulation device.

In one or more additional aspects of the disclosure, a method is disclosed and includes placing a submersible device within an algae slurry contained within a pond of an algae bioreactor, the submersible device including a drive motor, one or more driven devices operatively coupled to the drive motor, a circulation device, and a computer system that controls operation of the drive motor and the circulation device. The method may further include operating the drive motor to actuate one or more driven devices and thereby moving the submersible device within the pond, circulating the algae slurry through the submersible device with the circulation device, and discharging the algae slurry back into the pond from a discharge port provided on the submersible device.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION OF THE INVENTION

The present disclosure is related to algae cultivation for the production of biofuels and, more particularly, to a mixing and/or collection device submersible in an algae slurry of an algae bioreactor and operable to mix and aerate the algae slurry while filtering out particulate matter and harvesting algae of a predetermined size.

Figure 1A:
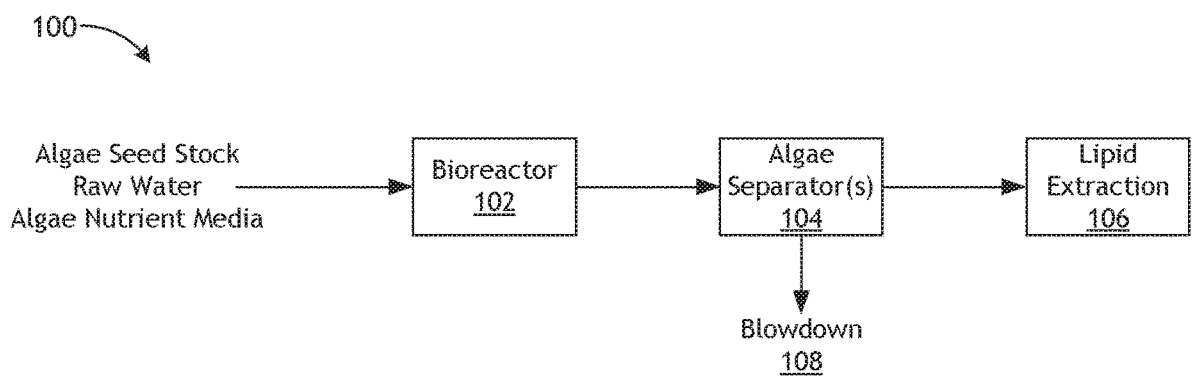
FIG. 1A is an example system for growing and harvesting algae for biofuel production.

FIG. 1A is an example system 100 that may be used to grow and harvest algae for biofuel production. As illustrated, the system 100 includes a bioreactor 102, which may comprise an open raceway pond, but the principles of the present disclosure may also be applicable to tubular-type enclosed or open reactors. The bioreactor 102 may be fed with raw water (e.g., salt water, ocean water, fresh water, etc.) to help create an algae slurry.

The bioreactor 102 is designed to contain the algae slurry. As used herein, the term "algae slurry," and grammatical variants thereof, refer to a flowable liquid comprising at least water, algae cells, and algae nutrient media, discussed in further detail hereinbelow. A prepared algae seed stock may be added to the raw water in the bioreactor 102, and algae nutrient media may be added to prepare the algae slurry for the cultivation and growth of algae. The algae nutrient media may comprise at least nitrogen (e.g., in the form of ammonia (including ammonium), nitrate, nitrite, or organic compounds containing nitrogen, such as urea) and phosphorous. Other elemental micronutrients may also be included, such as potassium, iron, manganese, copper, zinc, molybdenum, vanadium, boron, chloride, cobalt, silicon, and the like, and any combination thereof. The order in which the algae seed stock and the algae nutrient media are added to the raw water in the bioreactor 102 is not critical and either may be added before the other or they may be added simultaneously, without departing from the scope of the present disclosure.

The algae slurry may reside in the bioreactor 102 for a predetermined amount of time or until the algae matures and is ready for harvesting. Typical residence time in the bioreactor 102 can range between about 2 days and about 20 days. Once the algae matures and is otherwise ready for harvesting, the algae slurry is extracted from the bioreactor 102 and pumped to one or more algae-water separators 104 to be harvested and dewatered, during which process the algae in algae slurry is generally separated from the water. The algae-water separator(s) 104 may comprise any known separator, filter, or dewatering system known, and can include any combination thereof.

The separated algae is then conveyed downstream for lipid extraction 106 in preparation for biofuel production and other oil-based products. Various processing methods exist for harvesting cultivated algal biomass to extract lipids therefrom for the production of fuel and other oil-based products. Moreover, harvesting cultivated algal biomass can be used to produce non-fuel or non-oil-based products, including nutraceuticals, pharmaceuticals, cosmetics, chemicals (e.g., paints, dyes, and colorants), fertilizer and animal feed, and the like. Such methods traditionally include the addition of chemicals or the use of mechanical equipment to physically separate algae from the remaining components of a water slurry.

The separated water can be purged from the system 100 via a blowdown stream 108 and discharged into the environment or reused for another application. In some cases, the separated water purged via the blowdown stream 108 is conveyed to a wastewater treatment plant for treatment so that the separated water can be discharged into the environment with minimal impact.

Figure 1B:
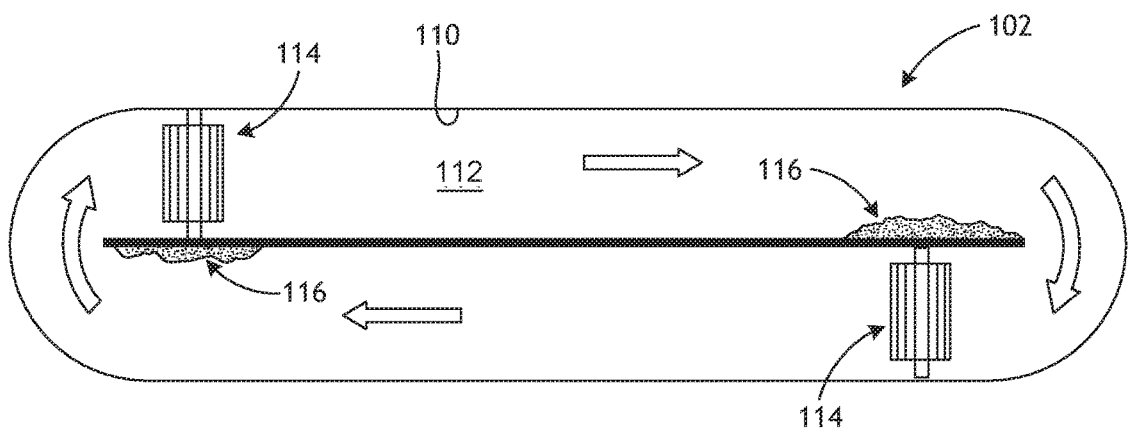
FIG. 1B is a schematic diagram of an example algae pond that may incorporate the principles of the present disclosure.

FIG. 1B is a schematic diagram of one example of the bioreactor 102 of FIG. 1A that may incorporate the principles of the present disclosure. In the illustrated embodiment, the bioreactor 102 comprises a "raceway" pond. Consequently, the bioreactor 102 will be referred to herein as the "pond 102." As illustrated, the pond 102 exhibits a generally pill-shaped perimeter and provides a single, closed-loop recirculation channel 110. The principles of the present disclosure, however, are equally applicable to ponds that exhibit other geometric shapes, such as circular, ovoid, polygonal (e.g., triangular, square, rectangular, etc.), or any combination thereof.

The pond 102 is designed to contain an algae slurry 112. In some embodiments, the depth of the algae slurry 112 within the pond 102 may be about 12 inches (in.) to facilitate sufficient sunlight penetration needed for algae growth. In other embodiments, however, the depth of the algae slurry 112 may be greater or less than 12 in., without departing from the scope of the disclosure.

Algal sources for the algae growing within the algae slurry 112 can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui,* and *Chlamydomonas reinhardtii.* Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella,* and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya,*

*Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

The pond 102 may include one or more paddlewheels 114 (two shown), or another suitable powered mechanical device, strategically placed in the pond 102 to facilitate continuous or intermittent circulation of the algae slurry 112 within the channel 110. The paddlewheels 114 also operate to mix the algae slurry 112 and thereby help keep the algae properly suspended within the algae slurry 112, which allows the algae to receive sufficient photonic energy from the sun for growth. This also helps prevent sedimentation of the algae cells contained within the algae slurry 112. Even with efficient paddlewheels 114 circulating the algae slurry 112, however, ash, debris, and other particulate matter (referred to herein as debris 116) often accumulate in one or more dead zones in the channel 110. In the illustrated example, for instance, the debris 116 is shown generally at the ends of the channel 110. The location of the debris 116 is not meant to limit the scope of the disclosure, rather those skilled in the art will readily appreciate that the debris 116 may collect at any location within the channel 110, without departing from the scope of the present disclosure.

The paddlewheels 114 require a large amount of power to operate and maintain the algae slurry 112 circulating and the algae properly suspended therein. Furthermore, once the algae concentration within the algae slurry 112 reaches a predetermined threshold (e.g., ~1000 ppm in water), the algae slurry 112 is pumped from the pond 102 to a harvesting facility, which also requires a large amount of power. After separating the algae from the water for further processing, the remaining water is typically pumped back to the pond 102 to start the next batch of algae growth, which process requires even more power. As a consequence, the energy consumption for algae growth (including cleaning and mixing) and harvesting can be significant, and can be approximately 40% of the total energy required to grow, harvest, and obtain viable algae for biofuel production.

According to embodiments of the present disclosure, a submersible or semisubmersible mixing device may be used in the pond 102 to simultaneously mix and filter the algae slurry 112 to remove debris 116, and subsequently collect mature algae when ready for harvesting. Consequently, the submersible device(s) may help increase algae growth rate by continuously mixing the algae slurry 112 and thereby allowing generated oxygen (O2) to be released. The submersible device(s) described herein may save energy by eliminating the need to circulate the algae slurry 112 from the pond 102 to a harvesting facility and back to the pond 102 for regeneration. Instead, only a fraction of the water is removed when the algae is harvested. The submersible device(s) described herein may also help increase the harvested algae concentration from approximately 1000 ppm in water to one or more orders of magnitude larger, which eliminates one or more harvesting steps and thereby saves a large amount of energy. In some cases, the submersible device(s) described herein may be capable of reducing the overall energy consumption for algae biofuel production by up to 50% or more.

Figure 2:
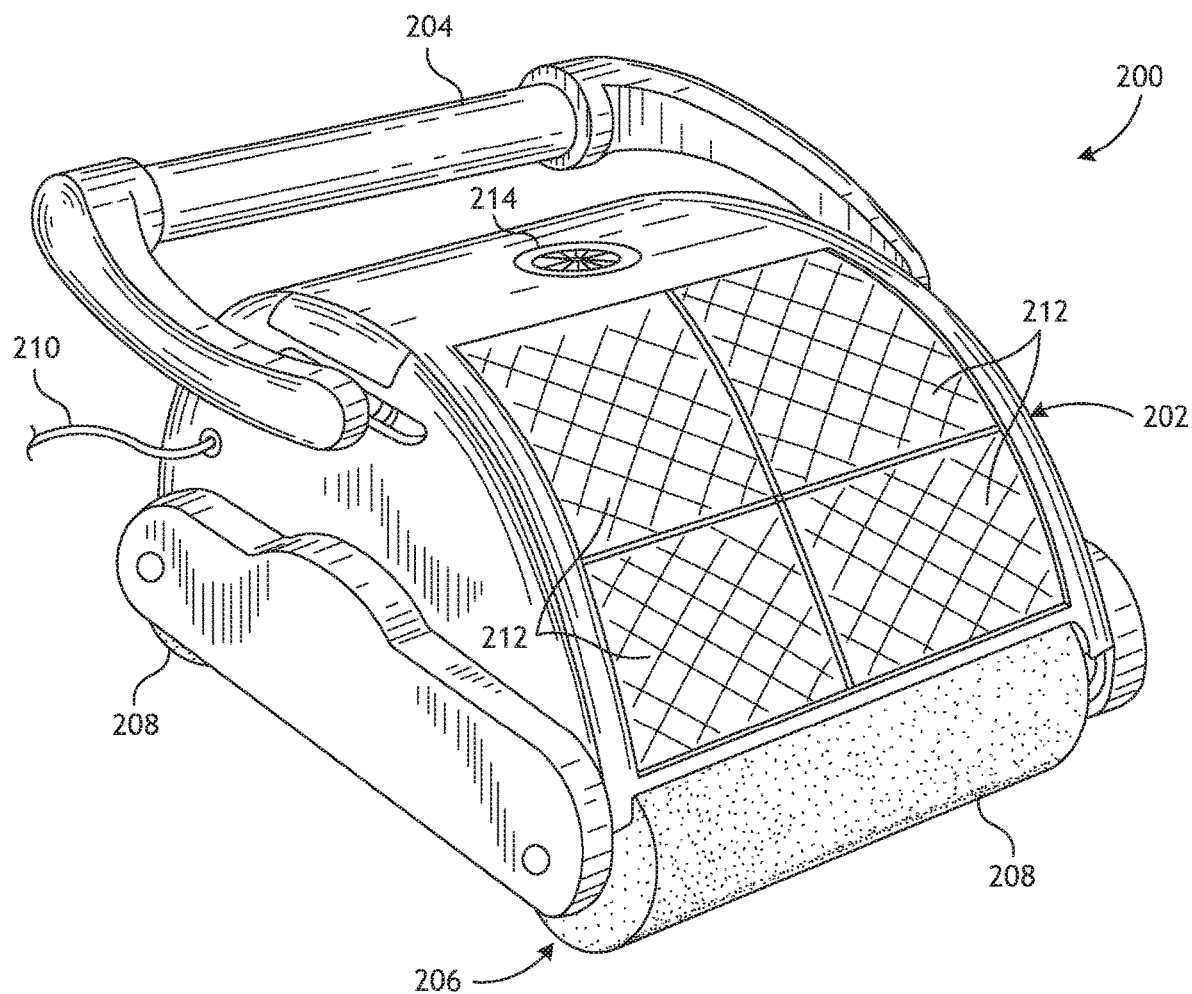
FIG. 2 is an isometric view of an example submersible device that may be used in accordance with the principles of the present disclosure.

FIG. 2 is an isometric view of an example submersible device 200 that may be used in accordance with the principles of the present disclosure. The submersible device 200 may capable of being fully or partially submerged in the pond 102 (FIG. 1) and traversing the channel 110 (FIG. 1) to perform various functions, as described herein below. In some embodiments, the submersible device 200 may be immersed in the algae slurry 112 (FIG. 1) and configured to travel along and operate at the bottom of the pond 102. In other embodiments, however, the submersible device 200 may be at least partially buoyant and otherwise capable of operating at any depth within the algae slurry 112, including on the surface of the algae slurry 112.

As illustrated, the submersible device 200 includes a housing 202 that contains various electronic and mechanical components used to operate the submersible device 200 and to perform the functions described herein. While depicted as having a particular shape and geometry, the housing 202 may exhibit any suitable shape or geometry, without departing from the scope of the disclosure. In some embodiments, the housing 202 may be hermetically sealed except at locations where fluid flows through the submersible device 200, as will be discussed below. In other embodiments, however, the housing 202 may not be entirely sealed but may nonetheless be capable of being immersed in the algae slurry 112 without causing damage to any internal electronic or mechanical parts. In at least one embodiment, a handle 204 may be coupled to the housing 202 to provide a grasping location for a user to transport, move, or manipulate the orientation of the submersible device 200.

The submersible device 200 may include a drive means 206 operatively coupled to the housing 202 to provide (facilitate) mobility to the submersible device 200. The drive means 206 may include at least one drive motor (not shown) arranged within the housing 202 and operable to actuate one or more driven devices that cause the submersible device 200 to move within the pond 102 (FIG. 1). In some embodiments, for example, the driven device may comprise one or more wheels or endless tracks (or a combination thereof) engageable with the bottom of the pond 102 (FIG. 1). In such embodiments, the drive motor may be configured to drive the wheels or endless tracks (or a combination thereof) to impel the submersible device 200 through the algae slurry 112 (FIG. 1).

In other embodiments, as illustrated, the driven device may comprise one or more brushes 208 (two shown) that contact the bottom of the pond 102. In such embodiments, the drive means 206 may cause the brushes 208 to rotate on corresponding axles and thereby impel the submersible device 200 through the algae slurry 112 while simultaneously cleaning the bottom of the channel 110 (FIG. 1). In yet other embodiments, the driven devices may comprise one or more jets of water that discharge fluid jets from associated ports located on the housing 202. In such embodiments, the drive means 206 may strategically actuate the jets to maneuver the submersible device 200 within the algae slurry 112. In even further embodiments, the driven devices may comprise a combination of any of the foregoing examples, and the drive means 206 may be configured to cooperatively operate the given combination, without departing from the scope of the disclosure. In some embodiments, the drive means 206 may be operated autonomously, as discussed in more detail below.

The submersible device 200 may be powered in a variety of different ways. In some embodiments, as illustrated, a power cable or cord 210 may extend from the submersible device 200 to be communicably coupled to a low-voltage power source outside of the pond 102 (FIG. 1), such as a conventional wall outlet. In other embodiments, or in addition thereto, the submersible device 200 may include one or more rechargeable batteries (not shown) arranged within the housing 202, such as within a waterproof or water-resistant floating case. In embodiments that also include the power cord 210, the battery(ies) may be recharged as needed through electrical power derived from the power cord 210. In other embodiments, however, the batteries may be removable from the housing 202 to be recharged separately. In yet other embodiments, the submersible device 200 may be maneuvered (manually or automatically) to a docking station where corresponding electrical contacts on the housing 202 and the docking station may engage to facilitate electrical power transfer to recharge the batteries.

In even further embodiments, one or more photovoltaic solar panels 212 may be coupled to and otherwise arranged on the housing 202 to generate electricity from the sun. In such embodiments, the depth of the algae slurry 112 (FIG. 1) may be at a level that enables sufficient photonic impingement on the solar panels 212 through a portion of the algae slurry 112. The electricity generated by the solar panels 212 may be used to recharge the batteries and/or directly power the submersible device 200. As will be appreciated, the solar panels 212 may allow the submersible device 200 to continuously operate and move in the pond 102 (FIG. 1) and thereby maximize efficiency. Moreover, any of the foregoing examples of powering the submersible device 200 may be used in any combination, without departing from the scope of the disclosure.

The submersible device 200 may further include a discharge port 214 coupled to or otherwise defined by the housing 202. The discharge port 214 may provide a location where fluid drawn into the housing 202 during operation of the mixing device 200 may be ejected from the housing 202. As described below, the algae slurry 112 (FIG. 1) may be drawn into the housing 202 at or near the bottom of the housing 202 and ejected from the housing 202 via the discharge port 214 to help mix and rotate the algae slurry 112 and thereby also ensure that the algae stays properly suspended within the algae slurry 112. Moreover, the discharge port 214 may be in fluid communication with one or more filter cartridges (not shown) arranged within the housing 202 that operate to filter the algae slurry 112 as it passes therethrough. Depending on the operational mode of the submersible device 200, circulating the algae slurry 112 through the submersible device 200 may help remove the debris 116 (FIG. 1) and/or harvest mature algae of a predetermined size.

Figure 3:
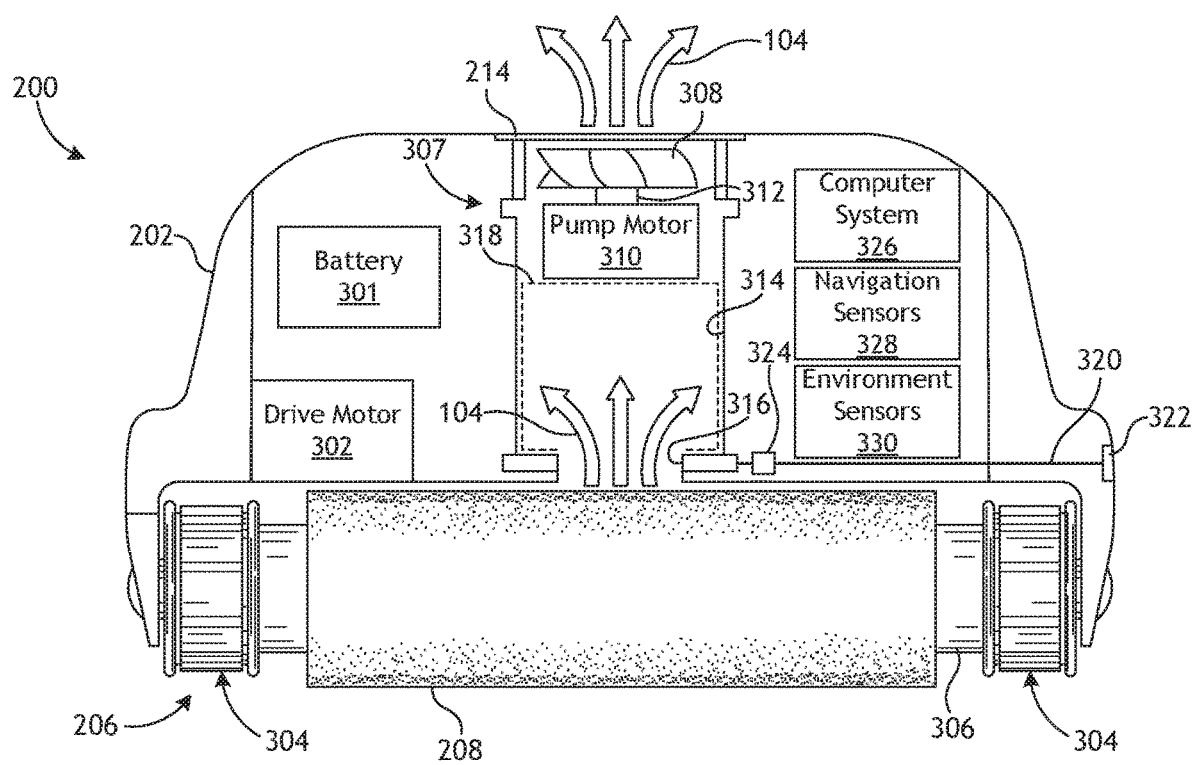
FIG. 3 is a schematic diagram of the interior of the mixing device of FIG. 2, according to one or more embodiments.

FIG. 3 is a schematic diagram of the interior of the submersible device 200, according to one or more embodiments. As illustrated, the submersible device 200 includes one or more batteries 301. The battery 301 may provide electrical power to various component parts of the submersible device 200, or alternatively electrical power may come from the solar panels 212 (FIG. 2). As indicated above, the battery 301 can be rechargeable via the power cord 210 (FIG. 2), through electrical power derived from the solar panels 212 (FIG. 2), or by being removed from the housing 202 and recharged separately. In other embodiments, however, the battery 301 may not be rechargeable but instead replaced with a new battery when the electrical charge is exhausted.

The submersible device 200 further includes a drive motor 302 arranged within the housing 202 and operable to operate the drive means 204, which causes the submersible device 200 to move within the pond 102 (FIG. 1). Electrical power needed to operate the drive motor 302 may come from the battery 301, or alternatively from the solar panels 212 (FIG. 2). In the illustrated embodiment, the drive means 204 includes driven devices in the form of one or more wheels or endless tracks 304 (two shown) mounted to a rotatable axle 306. The brush 208 may also be mounted to the axle 306 and may be rotatable therewith during operation. In such embodiments, the drive motor 302 may cause actuation of the wheels and/or endless tracks 304 while simultaneously causing the brush(es) 208 to rotate and thereby clean the bottom of the channel 110 (FIG. 1).

The submersible device 200 may further include a circulation device 307 operable to circulate the algae slurry 112 through the housing 202 and discharge the algae slurry 112 during operation. Electrical power needed to operate the circulation device 307 may come from the battery 301, or alternatively from the solar panels 212 (FIG. 2). In some embodiments, the circulation device 307 may include an impeller 308 and a pump motor 310 operatively coupled to the impeller 308 via a drive shaft 312. The pump motor 310 may be powered by the battery 301 in one or more embodiments, but may alternatively be powered by the solar panels 212. Operation of the pump motor 310 drives the drive shaft 312 and causes the impeller 308 to rotate. As the impeller 308 rotates, the algae slurry 112 is drawn into a filter chamber 314 within the housing 202 via an inlet 316 defined in the housing 202. The algae slurry 112 is able to circulate through the filter chamber 314 and exit the filter chamber 314 via the discharge port 214 located adjacent the impeller 308.

Continuously or intermittently circulating the algae slurry 112 through the filter chamber 314 and out the discharge port 214 using the circulation device 307 helps mix and rotate the algae slurry 112 and maintains the algae suspended within the algae slurry 112. As will be appreciated, the impeller 308 and the pump motor 310 are but one example of the circulation device 307 operable to circulate the algae slurry 112 through the housing 202. Those skilled in the art will readily recognize that various alternative designs and configurations of the circulation device 307 may be employed in the submersible device 200 suitable for circulating the algae slurry 112 through the housing 202, without departing from the scope of the disclosure. For example, while the impeller 308 is shown creating a vacuum within the filter chamber 314 to draw the algae slurry 112 into the filter 318, the circulation device 307 may alternatively include a means of pressurizing the algae slurry 112 and thereby pushing the algae slurry 112 into the filter chamber 314. In such embodiments, for example, the impeller 308 could be arranged at or near the inlet 316.

Since the submersible device 200 is able to move horizontally and vertically (e.g., buoyancy) within the channel 110 (FIG. 1), the submersible device 200 can provide both vertical and horizontal mixing of the algae slurry 112 throughout the pond 102 (FIG. 1) during operation. This is a significant advantage over the conventional paddlewheel mixers 114 (FIG. 1) positioned at stationary locations. In some embodiments, the circulation device 307 (e.g., the pump motor 310) may be operable at variable speeds to adjust the speed of mixing during operation as needed. This may prove advantageous since oftentimes certain areas or sections of the pond 102 may require more vigorous mixing as compared to other areas or sections.

In some embodiments, the circulation device 307 may include a filter 318 used to help remove the debris 116 (FIG. 1). In the illustrated embodiment, the filter 318 may be arranged within the filter chamber 314 and the incoming algae slurry 112 may be introduced into the filter 318 from the inlet 316. The filter 318 may comprise a mesh structure or membrane configured with openings small enough to retain particulate matter of a predetermined size, such as the debris 116. In such embodiments, the circulation device 307 may be operable to clean and filter the algae slurry 112 of the debris 116 as it circulates through the housing 202.

In some embodiments, the filter 318 may further be configured with openings sized to retain algae of a predetermined size. In such embodiments, the submersible device 200 may operate as an algae harvesting device as the algae slurry 112 circulates through the housing 202. In some embodiments, for instance, the filter 318 may have a mesh size rated to retain algae of the predetermined size. In at least one embodiment, the mesh size of the filter 318 may be about 2 microns to enable the filter to collect algae as small as 2 microns. Moreover, it is contemplated herein to define the cutoff of the filter 318 such that algae can be separated based on size differences between inoculum (i.e., small seed algae) and fully-grown algae. Similarly, smaller sizes of the filter 318 can be used to separate algae from the debris 116, while larger sizes of the filter 318 can separate other debris from the desired algae particle size ranges.

In some embodiments, the circulation device 307 may be designed and otherwise configured for backflush operation to avoid plugging of the filter 318 or otherwise to clean the filter 318 from lodged particulate debris. In such embodiments, the direction of flow through the housing 202 may be reversed and the reverse flow may dislodge particulate debris from the filter 318 and flow the particulate debris out of the housing 202 via the inlet 316. In some embodiments, backflushing operations may be undertaken as needed or otherwise on a predetermined and programmed schedule (e.g., once every 2 hours for 5 mins.).

In one or more embodiments, the submersible device 200 may include a bypass line 320 in fluid communication with the inlet 316. If the filter 318 becomes plugged and otherwise fluid is prevented from flowing through the filter 318, the algae slurry 112 may flow unobstructed through the bypass line 320 and thereby bypass the filtration portion of the circulation device 307. The bypass line 320 may terminate at a bypass discharge port 322 coupled to the housing 202, such as on a sidewall of the housing 202 or another suitable location. In some embodiments, the bypass line 320 may include a one-way valve 324 that allows flow through the bypass line 320 in only one direction. The valve 324 may comprise a pressure release valve, for example, that opens when a fluid pressure within the housing 202 (e.g., the filter chamber 314) surpasses a predetermined limit. Once the valve 324 opens, the algae slurry 112 may flow through the bypass line 320 and thereby bypass the plugged filter 318. As will be appreciated, this may help maintain fluid mixing rates in the pond 102 (FIG. 1) even when the filter 318 becomes clogged.

The submersible device 200 may further include an internal computer system 326 configured to control and regulate operation of the submersible device 200. In some embodiments, the battery 301 may provide electrical power to operate the computer system 326. The computer system 326 may include a pre-programmed microprocessor and electronic control device, which can include a controller and memory in wired or wireless communication with various component parts of the submersible device 200. In some embodiments, the memory of the computer system 326 may include pre-programmed stances of software instruction that allow the computer system 326 to operate the submersible device 200 autonomously. Accordingly, once the submersible device 200 is turned on, the computer system 326 may autonomously control operation thereof based on the pre-programmed instructions. For instance, the computer system 326 may communicate with the drive motor 302 to cause the submersible device 200 to move within the pond 102 (FIG. 1) to predetermined locations or otherwise as needed. Moreover, the computer system 326 may be in communication with the pump motor 310 to regulate operation of the circulation device 307 and any backflushing operations.

The submersible device 200 may further include one or more navigation sensors 328 in communication with the computer system 326 and used to help navigate and/or chart a path through the pond 102 (FIG. 1). In some embodiments, one or more of the navigation sensors 328 may comprise proximity sensors used to help navigate the submersible device 200 through the channel 110 (FIG. 1). Such navigation sensors 328 can be mechanical or electromechanical, such as infrared transmitters configured to receive signals reflected from the walls of the pond 102, or any other suitable sensor device. In some cases, movement of the submersible device 200 based on signals received by the proximity sensors may be entirely random and based solely on avoiding contact with side walls of the channel 110 or other obstructions. In at least one embodiment, the computer system 326 may be programmed with artificial intelligence to learn the shape and geometry of the pond 102 based on signals received by the proximity sensors.

One or more of the navigation sensors 328 may comprise position-locating sensors, such as a global position system (GPS). GPS units with marine and aircraft navigational systems are known in the art, and it is within the skill of the art to integrate the control of the submersible device 200 based on an algorithm with a starting set of coordinates provided by the GPS unit. For example, the submersible device 200 can be manually positioned at one location of the pond 102 (FIG. 1), as prescribed by the operating instructions and the GPS coordinate entered into the controller memory. The submersible device 200 can then be taken to a different location within the pond 102, e.g., the diagonally opposite corner of the pond 102, and those GPS coordinates may be entered. The program will then have sufficient information to determine an appropriate path for the submersible device 100 to follow in order to traverse substantially the entire bottom of the pond 102.

The entry of the coordinates can be in the way of a manual push button or other similar entry device based on a programming sequence provided to the user in a user's manual. A separate hand-held device that communicates with the controller, such as by IR signals or conductor wires, can be also utilized. The submersible device 100 may also include a floating antenna wire for receiving the GPS signals, or they can be transmitted through a receiver in the computer system 326. Once the submersible device 100 is positioned on the bottom surface of the pond 102 (FIG. 1) and activated, the algorithm that now includes the GPS coordinates can accurately direct the movement, turning, and distance changes necessary to cover the entire bottom surface of the pond 102 in an efficient pattern.

The submersible device 200 may further include one or more environment sensors 330 in communication with the computer system 326 and used to monitor conditions of the algae slurry 112. For example, the environment sensors 330 may be configured to measure and report various parameters of the algae slurry 112, such as pH level, salinity, $CO_2$ concentration, $O_2$ concentration, nutrient concentration, and any combination thereof. Based on the measurements provided by the environment sensors 330, the computer system 326 may determine that various nutrients (e.g., nitrogen, phosphorous, $CO_2$, etc.) are needed in the algae slurry 112 to promote efficient growth. In some embodiments, the required nutrients may be stored on-board on the submersible device 200 and a feeder system (not shown) may be activated to distribute the nutrients when needed. In at least one embodiment, for example, the submersible device 200 may be configured with the ability to sparge a gas (e.g., $CO_2$, nitrogen, etc.) into the algae slurry 112. In such embodiments, the submiersible device 200 may be tethered to a gas line that provides a steady flow of the gas as needed. In other embodiments, the computer system 326 may be in communication with a separate feeder system associated with the pond 102 (FIG. 1) that can be triggered to operate upon receiving appropriate signals from the computer system 326. In yet other embodiments, the computer system 326 may be programmed to send an alert to an operator to inform the operator of the potential need for additional nutrients. As will be appreciated, this will provide the ability to provide controlled and/or periodic addition of nutrients based on algae growth requirements.

In some embodiments, the environment sensors 330 may be configured to detect invasive species in the algae slurry 112 that might adversely affect algae growth. In such embodiments, the computer system 326 may be programmed to send an alert to the operator to inform the operator of the potential need for remedial action. In some embodiments, the environment sensors 330 may be "smart" sensors in that they may be able to measure concentrations of certain substances at a given location within the pond 102 (FIG. 1) and report to the computer system 326 that additional mixing or algae collecting should occur at that given location. In other embodiments, the computer system 326 may be able to make this determination based on the signals received by the environment sensors 330.

In example operation of the submersible device 200, the computer system 326 may be able to operate the submersible device 200 in a "cleaning mode" in which the circulation device 307 is operating to aerate and mixes the algae slurry 112 as it traverses the channel 110 (FIG. 1). This allows the algae to get the proper amount of sunlight for photosynthesis and to discharge O2 as needed. While in the cleaning mode, the submersible device 200 may also filter the algae slurry 112 by circulating the algae slurry through the filter 318 and thereby remove the debris 116 that settles within the channel 110. As will be appreciated, this may reduce the cleaning interval within the pond 102 and improve overall hydrodynamics of the algae slurry 112 circulating within the channel 110.

When the algae is ready for harvesting, the computer system 326 may be programmed or otherwise configured to switch the submersible device 200 to a "collection mode" (alternately referred to as a "harvest mode"). In some embodiments, the environment sensors 330 may be able to sense the concentration of the algae in the algae slurry 112 and send this signal to the computer system 326 to trigger the switch to the collection mode. In other embodiments, or in addition thereto, the environment sensors 330 may be configured to measure the size of the algae and send a signal to the computer system 326 to trigger the switch to the collection mode when the measured algae exceed a predetermined size threshold. In the collection mode, the submersible device 200 may draw in the algae slurry 112 and algae of the predetermined size may be retained within the filter 318 for collection, while algae smaller than the predetermined size is discharged back into the algae slurry 112 via the discharge port 214.

In some embodiments, it may be necessary to change out the filter 318 used during the cleaning mode for a filter appropriate for the collection mode. In other embodiments, however, the filter 318 used for the cleaning and harvesting modes may be the same. As will be appreciated, the size of the filter 318 may be adjusted to collect predominantly mature algae during the collection mode. In some embodiments, when the filter 318 becomes full, the computer system 326 may be configured to send a signal to an operator indicating the same, and the operator can remove the filter to gather the collected algae. In at least one embodiment, when the filter 318 becomes full, the computer system 326 may be programmed to navigate the submersible device 200 to a "home" station where it can be emptied. Once emptied, the submersible device 200 may then return to the channel 110 to continue to collect additional algae. The gathered and collected algae may then be transported as a concentrated slurry ("broth") to further separation and upgrading processes in preparation for algae biofuel production. As will be appreciated, as compared to conventional harvesting methods for raceway ponds, this method of collecting the algae significantly reduces the amount of water removed from the pond 102 by orders of magnitude.

It should be noted that a plurality of submersible devices 200 may be used in a given pond 102 (FIG. 1) and otherwise form part of an algae bioreactor designed for the growth and harvesting of algae used for biofuel production. The plural submersible devices 200 may all include corresponding internal computer systems 326 capable of communicating one with another within the pond 102. In such embodiments, the plural submersible devices 200 may operate efficiently to mix, aerate, and clean the algae slurry 112 and subsequently harvest mature algae from the algae slurry, as generally described above. Moreover, in such embodiments, it is contemplated herein that some of the features and capabilities described above with respect to the submersible device 200 may be included in only some of the plural submersible devices 200, and the remaining features and capabilities may be included in others of the the plural submersible devices 200. In such applications, the plural submersible devices 200 can be operated in concert to execute the various tasks in a desired sequence to achieve optimal algae growth performance.

Embodiments Listing

The present disclosure provides, among others, the following embodiments, each of which may be considered as optionally including any alternate embodiments.

Clause 1. An algae bioreactor that includes a pond that contains an algae slurry comprising at least water and algae, and a submersible device submersible within the algae slurry and including a drive motor operable to actuate one or more driven devices that move the submersible device within the pond, a circulation device operable to circulate the algae slurry through the submersible device and discharge the algae slurry back into the pond from a discharge port provided on the submersible device, and a computer system that controls operation of the drive motor and the circulation device.

Clause 2. The algae bioreactor of Clause 1, wherein the submersible device is at least partially buoyant and capable of operating at any depth within the algae slurry.

Clause 3. The algae bioreactor of Clause 1 or Clause 2, further comprising a battery contained within the submersible device to provide electrical power the drive motor, the circulation device, and the computer system.

Clause 4. The algae bioreactor of any of the preceding Clauses, further comprising one or more photovoltaic solar panels arranged on a housing of the submersible device to generate and provide electrical power the drive motor, the circulation device, and the computer system.

Clause 5. The algae bioreactor of any of the preceding Clauses, wherein the circulation device includes a filter that removes debris and algae from the algae slurry circulating through the submersible device.

Clause 6. The algae bioreactor of any of Clauses 1 through 4, wherein the circulation device includes a filter and the circulation device is operable to circulate the algae slurry through the submersible device in reverse to backflush the filter.

Clause 7. The algae bioreactor of any of the preceding Clauses, further comprising one or more navigation sensors in communication with the computer system to help navigate the submersible device within the pond.

Clause 8. The algae bioreactor of any of the preceding Clauses, further comprising one or more environment sensors in communication with the computer system to monitor one or more parameters of the algae slurry.

Clause 9. A submersible device submersible within an algae slurry contained within a pond of an algae bioreactor, the submersible device including a drive motor operable to actuate one or more driven devices that move the submersible device within the pond, a circulation device operable to circulate the algae slurry through the submersible device and discharge the algae slurry back into the pond from a discharge port provided on the submersible device, and a computer system that controls operation of the drive motor and the circulation device.

Clause 10. The submersible device of Clause 9, wherein the one or more driven devices are selected from the group consisting of one or more wheels, endless tracks, one or more brushes, one or more jets of water, and any combination thereof.

Clause 11. The submersible device of Clause 9 or Clause 10, further comprising a battery contained within the submersible device to provide electrical power the drive motor, the circulation device, and the computer system.

Clause 12. The submersible device of any of Clauses 9 through 11, further comprising one or more photovoltaic solar panels arranged on a housing of the submersible device to generate and provide electrical power the drive motor, the circulation device, and the computer system.

Clause 13. The submersible device of any of Clauses 9 through 12, wherein the circulation device comprises an impeller and a pump motor that causes the impeller to rotate.

Clause 14. The submersible device of any of Clauses 9 through 13, wherein the circulation device includes a filter that removes debris and algae from the algae slurry circulating through the submersible device.

Clause 15. The submersible device of any of Clauses 9 through 14, further comprising one or more navigation sensors in communication with the computer system to help navigate the submersible device within the pond.

Clause 16. The submersible device of any of Clauses 9 through 15, further comprising one or more environment sensors in communication with the computer system to monitor one or more parameters of the algae slurry.

Clause 17. A method that includes placing a submersible device within an algae slurry contained within a pond of an algae bioreactor, the submersible device including a drive motor, one or more driven devices operatively coupled to the drive motor, a circulation device, and a computer system that controls operation of the drive motor and the circulation device. The method further including operating the drive motor to actuate one or more driven devices and thereby moving the submersible device within the pond, circulating the algae slurry through the submersible device with the circulation device, and discharging the algae slurry back into the pond from a discharge port provided on the submersible device.

Clause 18. The method of Clause 17, wherein the circulation device includes a filter and circulating the algae slurry through the submersible device comprises selectively removing debris or algae from the algae slurry with the filter as the algae slurry circulates through the submersible device.

Clause 19. The method of Clause 18, further comprising harvesting the algae from the filter.

Clause 20. The method of any of Clauses 17 through 19, further comprising navigating the submersible device within the pond using one or more navigation sensors in communication with the computer system.

Clause 21. The method of any of Clauses 17 through 20, further comprising monitoring one or more parameters of the algae slurry with one or more environment sensors in communication with the computer system.

Clause 22. The method of Clause 21, further comprising switching the submersible device to a collection mode when the one or more environment sensors detect a predetermined algae concentration in the algae slurry.

Clause 23. The method of Clause 21, further comprising switching the submersible device to a collection mode when the one or more environment sensors detect algae of a predetermined size or greater.

Clause 24. The method of Clause 21, wherein the one or more parameters of the algae slurry include a presence of nutrients in the algae slurry to promote efficient growth of the algae, and wherein the method further comprises detecting with the one or more environment sensors when a concentration of the nutrients falls below a predetermined level, and distributing additional nutrients into the algae slurry based on signals provided by the one or more environment sensors.

Clause 25. The method of Clause 21, further comprising detecting an invasive species in the algae slurry with the one or more environment sensors.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An algae bioreactor, comprising:
   a pond that contains an algae slurry comprising at least water and algae;
   a submersible device submersible within the algae slurry and including:
   a drive motor operable to actuate one or more driven devices that move the submersible device within the pond;
   a circulation device operable to circulate the algae slurry through the submersible device and discharge the algae slurry back into the pond from a discharge port provided on the submersible device;
   a computer system configured to control operation of the drive motor and the circulation device;
   a sensor in communication with the computer system and configured to measure a nutrient level in the algae slurry; and
   a nutrient storage container storing nutrients configured to promote growth of the algae in the pond, wherein the nutrient storage container is in communication with the computer system, and the computer system is configured to determine nutrients to be distributed into the pond in response to the nutrient level.

2. The algae bioreactor of claim 1, wherein the submersible device is at least partially buoyant and capable of operating at any depth within the algae slurry.

3. The algae bioreactor of claim 1, further comprising a battery contained within a body of the submersible device to provide electrical power the drive motor, the circulation device, and the computer system.

4. The algae bioreactor of claim 1, further comprising one or more photovoltaic solar panels arranged on a housing of the submersible device to generate and provide electrical power to the drive motor, the circulation device, and the computer system.

5. The algae bioreactor of claim 1, wherein the circulation device includes a filter that removes debris and algae from the algae slurry circulating through the submersible device.

6. The algae bioreactor of claim 1, wherein the circulation device includes a filter and the circulation device is operable to circulate the algae slurry through the submersible device in reverse to backflush the filter.

7. The algae bioreactor of claim 1, further comprising one or more navigation sensors in communication with the computer system to help navigate the submersible device within the pond.

8. The algae bioreactor of claim 1, further comprising one or more environment sensors in communication with the computer system to monitor one or more parameters of the algae slurry.

9. A method, comprising:
   placing a submersible device within an algae slurry contained within a pond of an algae bioreactor, the submersible device including:
   a drive motor operable to actuate one or more driven devices that move the submersible device within the pond;
   a circulation device operable to circulate the algae slurry through the submersible device and discharge the algae slurry back into the pond from a discharge port provided on the submersible device;
   a computer system configured to control operation of the drive motor and the circulation device;
   a sensor in communication with the computer system and configured to measure a nutrient level in the algae slurry; and
   a nutrient storage container storing nutrients configured to promote growth of the algae in the pond, wherein the nutrient storage container is in communication with the computer system, and the computer system is configured to determine nutrients to be distributed into the pond in response to the nutrient level;
   operating the drive motor to actuate one or more driven devices and thereby moving the submersible device within the pond;
   circulating the algae slurry through the submersible device with the circulation device; and
   discharging the algae slurry back into the pond from the discharge port provided on the submersible device.

10. The method of claim 9, wherein the circulation device includes a filter and circulating the algae slurry through the submersible device comprises selectively removing debris or algae from the algae slurry with the filter as the algae slurry circulates through the submersible device.

11. The method of claim 10 further comprising harvesting the algae from the filter.

12. The method of claim 9, further comprising navigating the submersible device within the pond using one or more navigation sensors in communication with the computer system.

13. The method of claim 9, further comprising monitoring one or more parameters of the algae slurry with one or more environment sensors in communication with the computer system.

14. The method of claim 13, further comprising switching the submersible device to a collection mode when the one or more environment sensors detect a predetermined algae concentration in the algae slurry.

15. The method of claim 13, further comprising switching the submersible device to a collection mode when the one or more environment sensors detect algae of a predetermined size or greater.

16. The method of claim 13, wherein the one or more parameters of the algae slurry include a presence of nutrients in the algae slurry to promote efficient growth of the algae, and wherein the method further comprises:
   detecting with the one or more environment sensors when a concentration of the nutrients falls below a predetermined level; and
   distributing additional nutrients into the algae slurry based on signals provided by the one or more environment sensors.

17. The method of claim 13, further comprising detecting an invasive species in the algae slurry with the one or more environment sensors.

* * * * *